(12) United States Patent
Blase et al.

(10) Patent No.: US 11,527,863 B2
(45) Date of Patent: Dec. 13, 2022

(54) METHOD FOR EMITTING LASER LIGHT

(71) Applicant: Robert Bosch GmbH, Stuttgart (DE)

(72) Inventors: Benjamin Blase, Bietigheim-Bissingen (DE); Nico Heussner, Karlsruhe (DE); Raimund Reppich, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 107 days.

(21) Appl. No.: 16/963,670

(22) PCT Filed: Jan. 16, 2019

(86) PCT No.: PCT/EP2019/051004
§ 371 (c)(1),
(2) Date: Jul. 21, 2020

(87) PCT Pub. No.: WO2019/149523
PCT Pub. Date: Aug. 8, 2019

(65) Prior Publication Data
US 2021/0075183 A1 Mar. 11, 2021

(30) Foreign Application Priority Data
Feb. 1, 2018 (DE) .......................... 102018201508.2

(51) Int. Cl.
*H01S 3/11* (2006.01)
*A61F 9/008* (2006.01)

(52) U.S. Cl.
CPC .............. *H01S 3/11* (2013.01); *A61F 9/008* (2013.01)

(58) Field of Classification Search
CPC ............ H01S 3/11; A61F 9/008; G01S 17/00
See application file for complete search history.

(56) References Cited

U.S. PATENT DOCUMENTS

| | | | |
|---|---|---|---|
| 9,579,153 B2* | 2/2017 | Dick | A61B 18/20 |
| 2001/0010003 A1 | 7/2001 | Lai | |
| 2012/0296318 A1 | 11/2012 | Wellhofer et al. | |
| 2014/0204396 A1 | 7/2014 | Giger et al. | |
| 2015/0230978 A1* | 8/2015 | Vogler | H01S 5/0085 606/4 |
| 2017/0045721 A1* | 2/2017 | Charles | A61B 3/14 |

(Continued)

FOREIGN PATENT DOCUMENTS

| | | |
|---|---|---|
| DE | 102007018366 A1 | 10/2007 |
| DE | 102011103181 A1 | 12/2011 |

(Continued)

OTHER PUBLICATIONS

International Search Report for PCT/EP2019/051004, dated Jul. 25, 2019.

*Primary Examiner* — Gary Jackson
*Assistant Examiner* — Sebastian X Lukjan
(74) *Attorney, Agent, or Firm* — Norton Rose Fulbright US LLP; Gerard Messina

(57) ABSTRACT

A method for emitting laser light in the form of laser pulses, including the steps: planning a laser pulse based on pulse parameters, checking whether laser pulses which were emitted within a predefined preceding time interval, together with the planned pulse, meet a predefined energy criterion, and emitting the planned laser pulse with the aid of an emitting unit if the energy criterion is met, and not emitting the planned laser pulse or reducing a power of the laser pulse if the energy criterion is not met.

20 Claims, 3 Drawing Sheets

(56) References Cited

U.S. PATENT DOCUMENTS

2017/0307758 A1   10/2017  Pei et al.
2017/0307759 A1*  10/2017  Pei ........................ B60R 11/04
2018/0259623 A1*   9/2018  Donovan .............. G01S 7/4815

FOREIGN PATENT DOCUMENTS

| JP | 2002054989 A | 2/2002 |
| JP | 2002344075 A | 11/2002 |
| JP | 2007529271 A | 10/2007 |
| JP | 2009279631 A | 12/2009 |
| WO | 03101325 A1 | 12/2003 |
| WO | 2007034875 A1 | 3/2007 |

\* cited by examiner

METHOD FOR EMITTING LASER LIGHT

FIELD

The present invention relates to a method for emitting laser light. In particular, the method ensures that an eye safety is achieved during the emission of the laser light. The present invention furthermore relates to a computer program product as well as to a laser system for emitting laser light.

BACKGROUND INFORMATION

Conventional, optically active sensors and actuators may use an active light source, such as, in particular, a laser. Such sensors and actuators have to be designed in such a way that the maximum emitted light output is not able to damage a human eyesight even in an unfavorable spatial and temporal combination.

International standards on eye safety exist for this purpose, based on which, as a function of the parameters of the light emission, light output limiting values may be derived for the guaranteed adherence to the eye safety in all possible operating scenarios. Assuming the most unfavorable spatial and temporal combination of such a system at any point in time causes the parameters of the light emissions to be operated below the damage threshold during normal operation. In particular, no consideration of the actual operating behavior takes place, so that the emission of laser light follows a control system which includes fixedly predefined limiting values.

A system for operating a laser device is described in German Patent Application No. DE 10 2007 018 366. It is provided in the process that a control system is present, which supplies a laser pulse sequence signal having an established duty cycle and an established power level, which, in particular, meets requirements with regard to an eye safety limit.

SUMMARY

By actively regulating operating parameters, the present invention makes it possible to ensure the eye safety for the respective instantaneous hazard situation. In this way, a higher power may be output during regular operation than is possible in the related art. This is advantageous both for optical actuators, such as laser projectors, and for optically active sensors, such as LIDAR systems. Specifically, the active regulation either actively intercepts certain worst case scenarios, so that the permissible power increases, or an adaptive adjustment of the output power is carried out. The latter results, in particular, in a reduction of the emission power if the operating behavior is progressing in the direction of a worst case scenario.

An example method according to the present invention for emitting laser light in the form of laser pulses includes the following steps:

Initially, a planning of a laser pulse based on pulse parameters is carried out. The pulse parameters represent properties of the laser pulse, based on which an emitting unit has to be activated to emit the laser pulse. Thereafter, a check is carried out as to whether laser pulses which were emitted within a predefined preceding time interval, together with the planned pulse, meet a predefined energy criterion. The energy criterion ensures, in particular, an eye safety. This means that the predefined energy criterion includes such energy limiting values which are necessary for an eye safety. In this way, it is checked according to the present invention for each pulse whether the pulse adheres to the energy criterion for the eye safety. The actually emitted preceding pulses are resorted to in the process, so that a very precise picture about the previously emitted energy in the form of laser light may be ascertained. Finally, the emission of the planned laser pulse is carried out with the aid of the emitting unit if the energy criterion is met. If, in contrast, the energy criterion is not met, the planned laser pulse is not emitted. As an alternative, a reduction of a power of the laser pulse takes place if the energy criterion is not met. This means that the pulse parameters can be changed if the energy criterion is not met, and a laser pulse having a lower power is emitted instead of the planned laser pulse. This means that it is checked for each laser pulse whether the emission of the planned laser pulse would result in a violation of the energy criterion, which would mean that eye safety may no longer be ensured. A constant monitoring of the laser-emitting system, in particular, of the emitting unit, thus takes place. While, in contrast thereto, common systems carry out one-time calculations for the eye safety, assuming worst-case scenarios, to establish the parameters for emission limits, and thus also the parameters for the laser-emitting system, in all operating states, an actually emitted radiation, in particular, together with a system state of the emitting unit, is registered within the scope of the present invention, to carry out calculations therefrom as to which parameters keep the laser-emitting system in an eye-safe state. These calculations are advantageously carried out in real time based on the measured parameters. This means that the method according to the present invention is carried out in real time for each planned laser pulse. In this way, a regulation takes place.

Preferred refinements of the present invention are described herein.

It is preferably provided that the energy criterion represents a maximum energy of the laser light that does not result in permanent damage to a human eye. In particular, known eye safety standards indicate the light output which is allowed to strike a human eye, without resulting in permanent damage. This maximum light output may be formed into an energy criterion which is adapted to a specific emitting unit. The energy criterion particularly advantageously encompasses three different rules: A first rule is an individual pulse criterion, which may be ensured by monitoring the pulse parameters of an individual laser pulse. The pulse parameters to be considered are, in particular, a pulse duration and a pulse energy. A second rule is a mean value criterion, which limits the sequence of laser pulses, which is also described as a pulse pattern hereafter. A time window of an arbitrary length is placed over the pulse pattern in the process, and the energy emitted therein is integrated. The released energy must not exceed a limit, which may be derived from the length of the time window. This process must apply to every duration between a maximum of $1 \times 10^{-7}$ s and 30,000 s, and for each starting point during the pulse pattern. A third rule is a reduction criterion, at which it is analyzed how many theoretical pulses of a certain length fit into the time window to be maximally considered from the second rule. A correction factor is calculated from the length of these quasi pulses and their number and is multiplied by the energy limit of the second rule.

In a further preferred specific embodiment of the present invention, it is provided that all laser pulses are discrete laser pulses. This simplifies the ascertainment and checking of the energy criterion. It was, in particular, described above that three different rules are to be adhered to. The adherence to these rules may, for example, be calculated according to a brute force method, in which each individual pulse is stored, and the time windows which are necessary for checking the adherence to the energy limits are calculated in a highly resource-intensive process. Moreover, in the case of scanning systems, the angle of reflection of the laser pulses has to additionally be taken into consideration, to be iterated not just across the entire time, but also across the entire angular range of the emission. To simplify this, it is provided that only discrete laser pulses are present, by which, in particular, no temporally constant radiated wave (continuous wave, cw) or a modulated beam is emitted. Particularly advantageously, a predefined minimum distance exists between two discrete laser pulses. This simplifies, in particular, the checking of the energy criterion since, in particular, the maximum number of laser pulses within a predefined time window has an upper limiting value due to the predefined minimum distance of the laser pulses. The emitted light output may furthermore be ascertained easily and with low complexity by integrating the individual energies of the laser pulses. In this way, a resource-conserving and rapid checking of the adherence or non-adherence to the energy criterion is made possible.

In one preferred specific embodiment of the present invention, it is provided that the energy criterion has a maximum value of a permitted pulse duration and/or of a pulse energy of the planned laser pulse. As an alternative or in addition, it is provided that the energy criterion has a minimum value of a distance between two laser pulses. This means that the energy criterion encompasses an individual pulse criterion as described above as the first rule. In particular, it is checked whether the individual planned laser pulse during emission would itself already violate the energy criterion. A consideration of the preceding emitted laser pulses is not necessary for this purpose.

Furthermore, it is advantageously provided that a predefined pulse pattern is emitted in a recurring manner. This means that a frame is present, which is always reflected in the emitted laser pulses. In particular, the recurring pulse pattern may be an image of a laser projector or a frame in a LIDAR sensor. In this way, a periodicity of the emitted laser light is achieved. This, in turn, results in a simplification of the check of the energy criterion since it is possible, in particular, to limit the second rule, as described above, to the checking of the light output of the recurring pulse pattern. In this way, it is possible to check in a resource-conserving and rapid manner whether the energy criterion is met.

The energy criterion particularly advantageously encompasses a maximum value of an emission energy of the entire pulse pattern. In this way, it is checked, in particular, for each pulse pattern whether a maximum value of a light output is adhered to. If the maximum value is reached, in particular, no further pulses of the pulse pattern are emitted. This means that planned laser pulses of the pulse pattern are not emitted. As an alternative, an approach of the maximum value may be identified, and the emission of further planned laser pulses of the pulse pattern may only be permitted under reduced emission energy.

This means that the energy of the individual planned laser pulses is reduced to emit all laser pulses of the pulse pattern, and nonetheless meet the maximum value of the emission energy of the pulse pattern.

The laser light is preferably emitted in a scanning manner at a changing solid angle. The solid angle is discretized in a grid made up of discrete pixels. For each pixel, a light output of each laser pulse striking the pixel is integrated to check that each pixel meets the energy criterion. In particular, such a calculation is also carried out for the planned laser pulse. Based on the discretization with the aid of pixels, it is also possible to discretize a maximum eye diameter of a human eye. In this way, the area across which the laser light may be incident into the human eye may be discretized by a number of pixels. From this, the maximum number of pixels which the individual laser pulses strike in the case of a scanning system may be ascertained. From this, it is possible, in turn, to derive easily and with low complexity how much light energy may strike an individual pixel to ensure eye safety. In this way, the energy criterion is ascertainable easily and with low complexity based on the discretization. In particular, a size of the pixels is considerably smaller than an eye area or the cross section of the emitted laser light. An average discretization error decreases with the pixel density, whereas the computing time and the resource expenditure increase. The emitted light output of a laser pulse is thus divided among each affected pixel. It is thus possible to ascertain, for each pixel, easily and with low complexity the light energy this pixel is exposed to in the case of an individual laser pulse or in the case of a pulse pattern.

Particularly advantageously, a time period is determined during which the laser light passes over a predefined eye opening area. The eye opening area represents the area through which the laser light is able to enter a human eye. The eye opening area is defined by the diameter of the pupil of the eye. During this time period, a pulse group of multiple laser pulses is emittable. The energy criterion advantageously encompasses a maximum value for the number of laser pulses of the pulse group and/or for a distance of two consecutive pulse groups.

The pulse parameters advantageously encompass a pulse point in time and/or a pulse energy and/or a pulse length and/or a pulse power and/or a pulse exit angle. The planned laser pulse is planned based on these parameters, and it is checked based on these parameters whether the planned laser pulse meets the energy criterion. Particularly advantageously, system parameters of the emitting unit may additionally be read out. Such system parameters encompass, in particular, an orientation, a system's own movement, in particular, vibrations and transverse acceleration, data of a distance sensor system, or instantaneous pieces of information about the lens system and beamforming. These system parameters provide information as to whether the system state has changed them, and whether and how the calculation of the eye safety has to be adapted.

The present invention furthermore relates to a computer program product. The computer program product includes program code for carrying out the above-described method stored on a machine-readable memory medium when the computer program product runs on a computing device. The computing device is advantageously a control unit of a laser-emitting system. For example, the computing device may be the control unit of a laser projector or of a LIDAR sensor.

The present invention also relates to a laser system for emitting laser light. An example laser system according to the present invention includes an emitting unit for emitting laser pulses based on pulse parameters. The pulse parameters correspond, in particular, to the above-described pulse parameters. The laser system furthermore includes a control unit for activating the emitting unit. The control unit is designed to carry out a method as described above. In particular, the control unit is a computing device, as defined above.

BRIEF DESCRIPTION OF THE DRAWINGS

Exemplary embodiments of the present invention are described hereafter in detail with reference to the figures.

DETAILED DESCRIPTION OF EXAMPLE EMBODIMENTS

Figure 1:
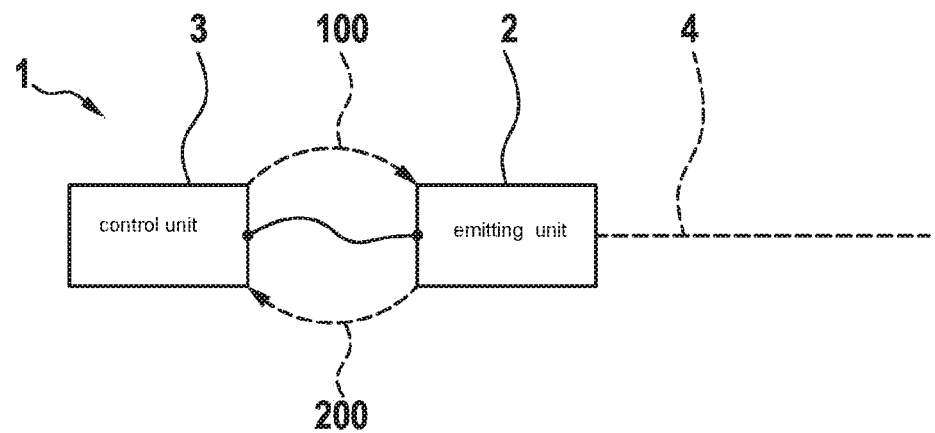
FIG. 1 shows a schematic view of a laser system according to one exemplary embodiment of the present invention.

FIG. 1 schematically shows a laser system 1 for emitting laser light 4. Laser system 1 includes an emitting unit 2 for emitting laser pulses based on pulse parameters. Only discrete laser pulses having a predefined minimum distance are emitted by emitting unit 2.

Laser system 1 furthermore includes a control unit 3. Control unit 3 is used to activate emitting unit 2. With the aid of a method according to one exemplary embodiment of the present invention, control unit 3 ensures that the emitted laser light 4 is eye-safe, i.e., the emitted laser light 4 cannot permanently damage a human eye. At the same time, an output power of laser light 4 is maximized.

Control unit 3 plans a laser pulse to be emitted by emitting unit 2, and activates emitting unit 2 using corresponding pulse parameters 100 for it to emit the laser pulse as laser light 4. Control unit 3 additionally checks in the process whether the planned laser pulse would violate a predefined energy criterion. If this is the case, either pulse parameters 100 are modified to reduce an output power of the planned laser pulse, or the emission of the planned laser pulse is entirely dispensed with.

To be able to check the adherence or non-adherence of the energy criterion, in particular, measuring parameters 200 are read out by emitting unit 2. These measuring parameters 200 encompass, in particular, pulse parameters 100 of the laser pulses already emitted, and additionally encompass system parameters. The pulse parameters are a pulse point in time and/or a pulse energy and/or a pulse length and/or a pulse power and/or an exit angle. The system parameters are, in particular, parameters such as an orientation and/or a system's own movement and/or data of a distance sensor system and/or instantaneous pieces of information about a lens system and beamforming. In the case of the system's own movement, in particular, vibration and/or transverse acceleration is/are determined. These system parameters allow conclusions to be drawn as to whether the system status has changed. Moreover, it may be ascertained based on the system parameters whether and how the calculation of the eye safety has to be adapted.

In general, the energy criterion must establish the maximum energy which a laser pulse emitted at any arbitrary point in time may have to ensure eye safety. The eye safety is advantageously checked based on three different rules:

A first rule represents an individual pulse criterion. In the case of the individual pulse criterion, it is checked whether the energy of the individual planned laser pulse is too high, so that the individual laser pulse itself would already result in a violation of the eye safety. The first rule may thus, in particular, be ensured by monitoring the pulse parameters of the planned laser pulses. In particular, a pulse duration and a pulse energy are checked.

A second rule is a mean value criterion, which limits the sequence of pulses of a pulse pattern. It is provided in the process that a sequence of laser pulses is considered a pulse pattern. A time window of an arbitrary length is placed over the pulse pattern in the process, and the energy emitted therein is integrated. The released energy must not exceed a limit, which is derived from the length of the time window. This process must apply to arbitrary durations and to arbitrary starting points.

A third rule is a reduction criterion, in which it is analyzed how many theoretical pulses of a certain length fit into the time window to be maximally considered from the second rule. A correction factor may be calculated from the length of these quasi pulses and their number, which is multiplied by the energy limit from the second rule.

The adherence to these rules may be checked by a brute force method, in which each individual pulse is stored, and individual time windows are calculated in a relatively resource-intensive process, based on which the energy limits may be checked. This, however, is not practical. It is therefore provided that emitting unit 2 only emits laser light 4 under the following conditions:

Only discrete laser pulses are emitted so that no continuous wave or a modulated beam is present. A predefined minimum pulse distance is present between two of these discrete laser pulses. The emission of laser light 4 takes place, in particular, at recurring pulse patterns, which means that laser light 4 has a periodicity. In particular, the laser light is thus made up of a succession of recurring pulse patterns. The pulse pattern may, for example, be the image of a laser projector or the frame of a LIDAR sensor.

Based on these simplifications, it is possible to check the energy criterion easily and with low complexity, in particular, taking the three aforementioned rules into consideration. For this purpose, a first temporal monitoring area is provided, which is derived from the periodicity of laser light 4. Based on each pulse pattern, a maximum emission energy may be ascertained, which is permitted for the eye safety. It is, in particular, made possible, for example, to start a dedicated integrator for each pulse pattern to ascertain the entire energy emitted in the pulse pattern. This energy must not exceed a limiting value, the limiting value being derivable from known eye safety standards. If this limiting value were to be exceeded by a planned laser pulse, either an output power of the laser pulse is reduced, or the emission of the laser pulse is entirely dispensed with. It is advantageously also provided that, in the event of an approach of the limiting value, control unit 3 reduces the output power of the planned laser pulses, even if the instantaneously planned laser pulse would not exceed the maximum value for the energy of the pulse pattern.

A second temporal monitoring area is derived from laser light 4 passing over a human eye placed in the projection space in a scanning system. In particular, emitting unit 2 is configured to emit the laser light at a variable angle. This results in a pulse group which could strike an eye in an eye pass-over. Based on a movement velocity, at which the angle of the emitted laser light 4 changes, it is thus possible to ascertain a maximum number of laser pulses which could strike the eye. In particular, the second monitoring area uses the maximum temporal duration of the eye pass-over for reference. In this way, an energy limit which the aforementioned pulse group is maximally permitted to have may be ascertained. The monitoring of the second monitoring area takes place similarly to the first monitoring area by an integrator, which integrates the energy of the laser pulses of the pulse group. The energy limit of the second temporal monitoring area may advantageously be derived from known eye safety standards.

A third temporal monitoring area uses an individual planned laser pulse and its distance from the preceding emitted laser pulse for reference. It has to be checked for each individual laser pulse here whether the planned pulse energy ensures eye safety or whether eye safety is no longer ensured by the aforementioned pulse energy. The same applies to a distance from a preceding emitted laser pulse, it also being possible to derive limiting values, which must be adhered to by the individual laser pulses, from known eye safety standards for these cases.

Figure 2:
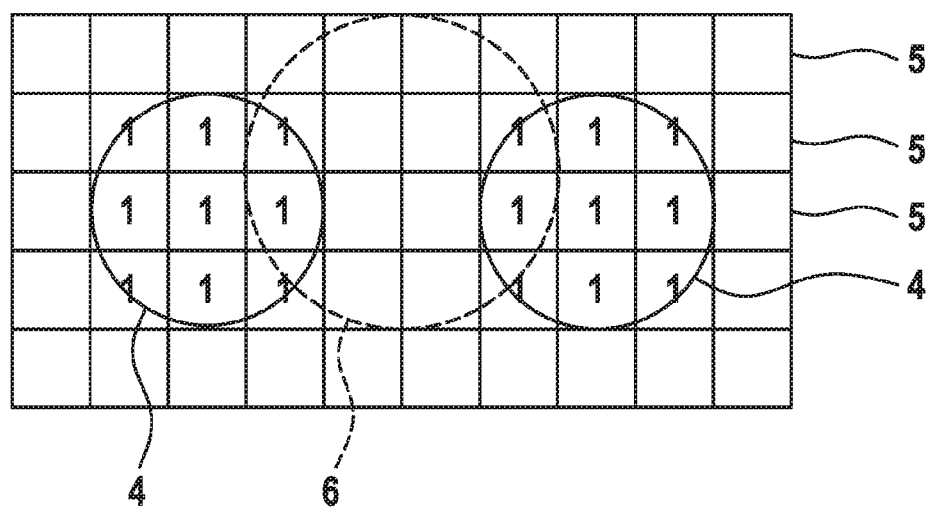
FIG. 2 shows a schematic view of a discretization of solid angles of the laser light emitted with the aid of the laser system from FIG. 1.

FIG. 2 schematically shows a discretization according to the exemplary embodiment of the present invention. This is necessary since the eye safety calculations always have to be carried out for the incident light in an eye diameter. As a result, a system is to be developed which calculates these parameters in a modular manner for every possible eye diameter placed in the angular space. A grid made up of discrete pixels 5 is therefore provided, pixels 5 having the size of a fraction of an eye opening area 6. Eye opening area 6 is determined by a maximum diameter of a pupil of an eye to be protected. The light output of laser light 4 is proportionately accumulated according to the three above-described temporal monitoring areas in the corresponding pixels 5 which are affected by laser light 4. The above-described calculation of the temporally accumulated light output within the meaning of the eye safety may take place for any possible spatial integral window of the size of an eye diameter. The average discretization error of such a system drops with the pixel density of the grid, whereas the computing time as well as the resource expenditure increase.

Figure 3:
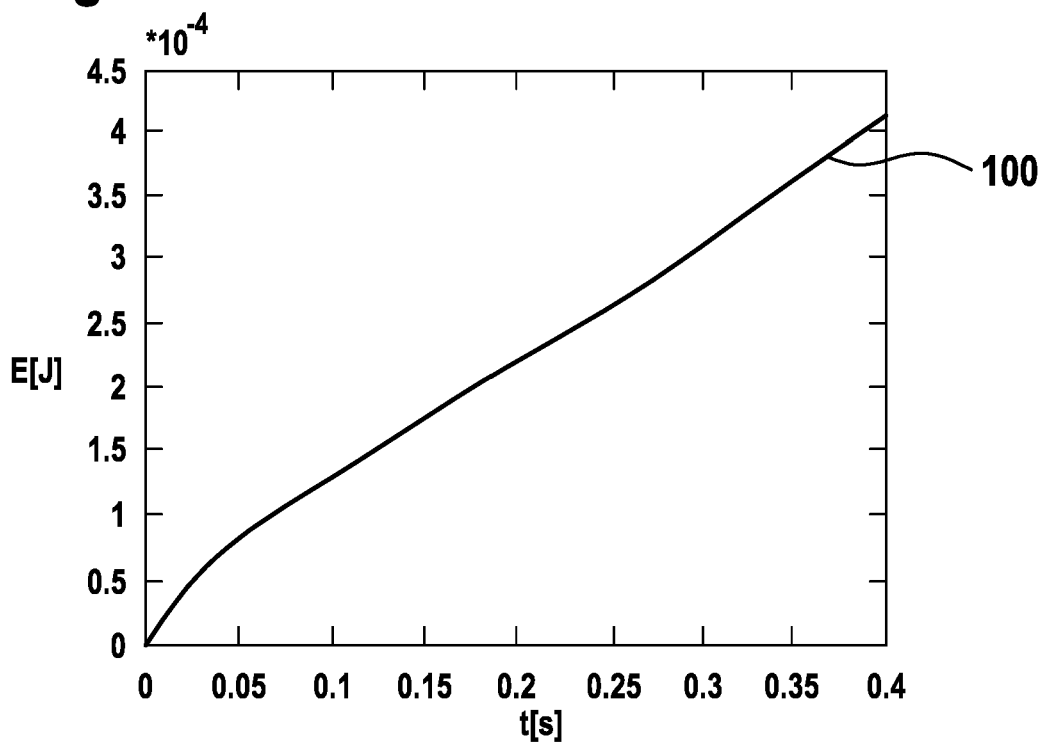
FIG. 3 shows a first schematic view of the derivation of the energy criterion.

FIGS. 3 through 6 schematically show an exemplary derivation of the energy criterion for laser light 4 having a wavelength of 905 nanometers. At this wavelength, the energy limit according to known eye safety standards initially increases over the duration of the considered time window at a root function, and consequently increases drastically in the beginning, but increasingly less toward the end. In addition, the correction factor from the above-described third rule takes effect starting at a certain time, so that the curve has a profile which is not easy to calculate. The curve of energy limit 100 is schematically represented in FIG. 3.

Initially, a first simplification area is ascertained, which relates to pulse patterns having a periodicity. This recurring time segment has a certain duration and a consistent emitted energy and is to be repeatable any arbitrary number of times, without violating the eye safety. The highest known limit is thus broken down linearly to the length of a pulse pattern. This highest known limit is the definition of the limit across the greatest possible time window. As a result of the linear break down, an energy limit 200 is established, which is permitted to be emitted per frame per angular range which the eye assumes. The angular range corresponds to the angular range of the emission angle at which laser light 4 is emitted by emitting unit 2.

A second area of the simplification relates to the assumption that it is the goal of laser system 1 to consecutively emit many laser pulses in a short time at a similar angular range. A pulse group is defined for this purpose, which establishes the maximum number of laser pulses which may be consecutively emitted with the predefined minimum pulse distance. The maximum emittable pulse number 300 is shown in FIG. 5.

Figure 4:
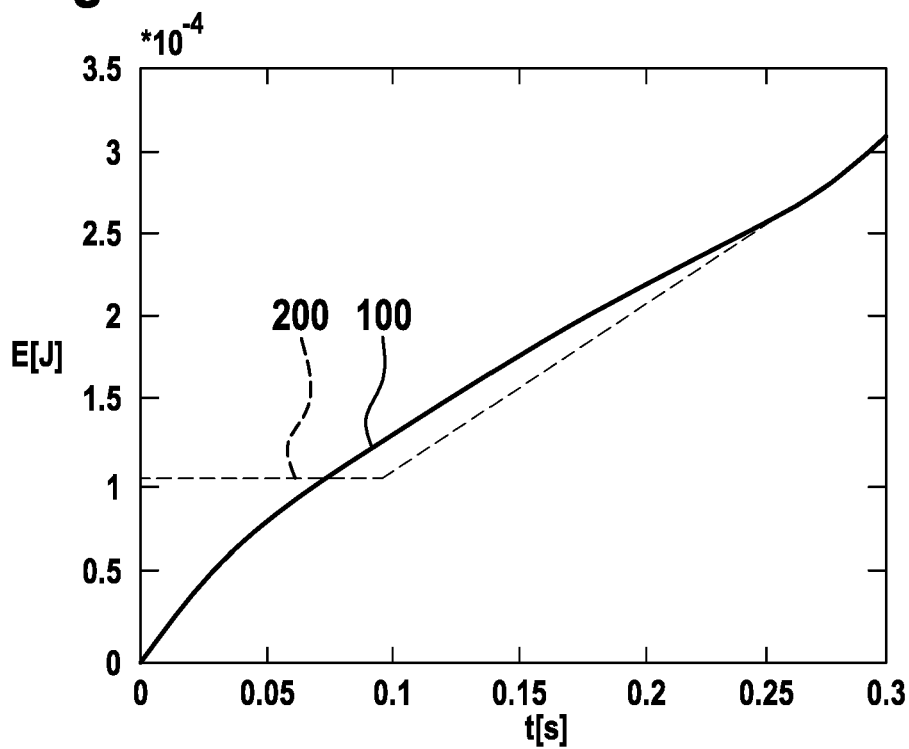
FIG. 4 shows a second schematic view of the derivation of the energy criterion.
Figure 5:
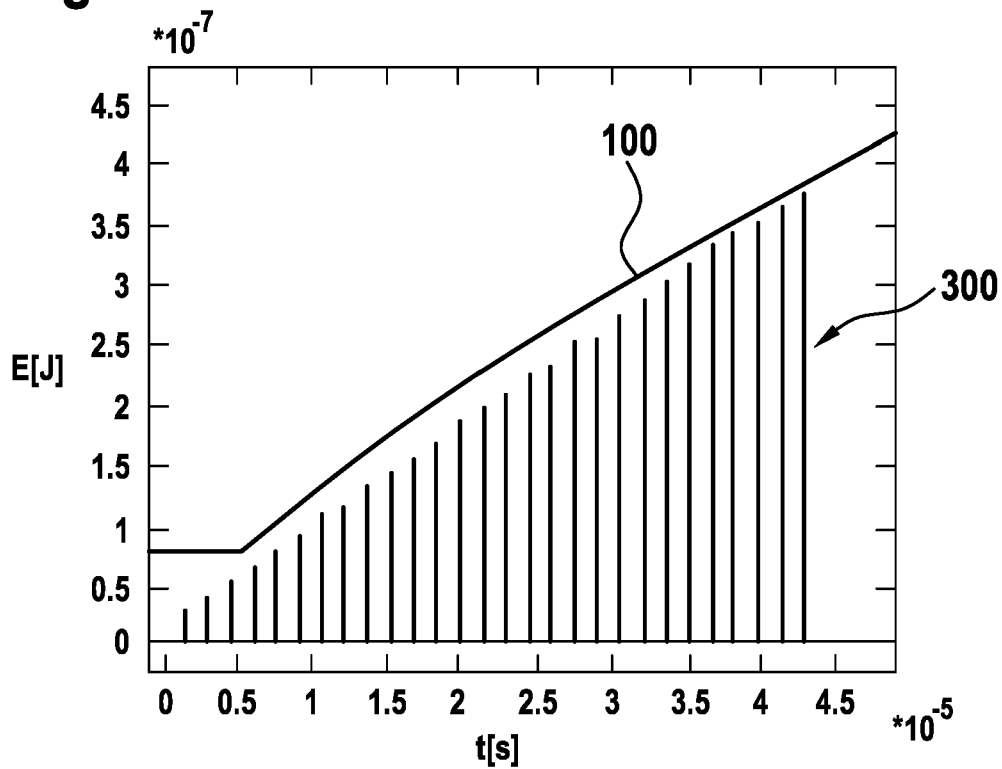
FIG. 5 shows a third schematic view of the derivation of the energy criterion.

A third area results from the combination of the first area, as shown in FIG. 4, and of the second area, as shown in FIG. 5. In this way, a minimum area of the eye safety standard is covered by the pulse group, and an absolute energy limit per pulse pattern is established. From this, it is possible to derive how long a wait is necessary after each pulse group not to exceed energy limit 100 within a pulse pattern.

Figure 6:
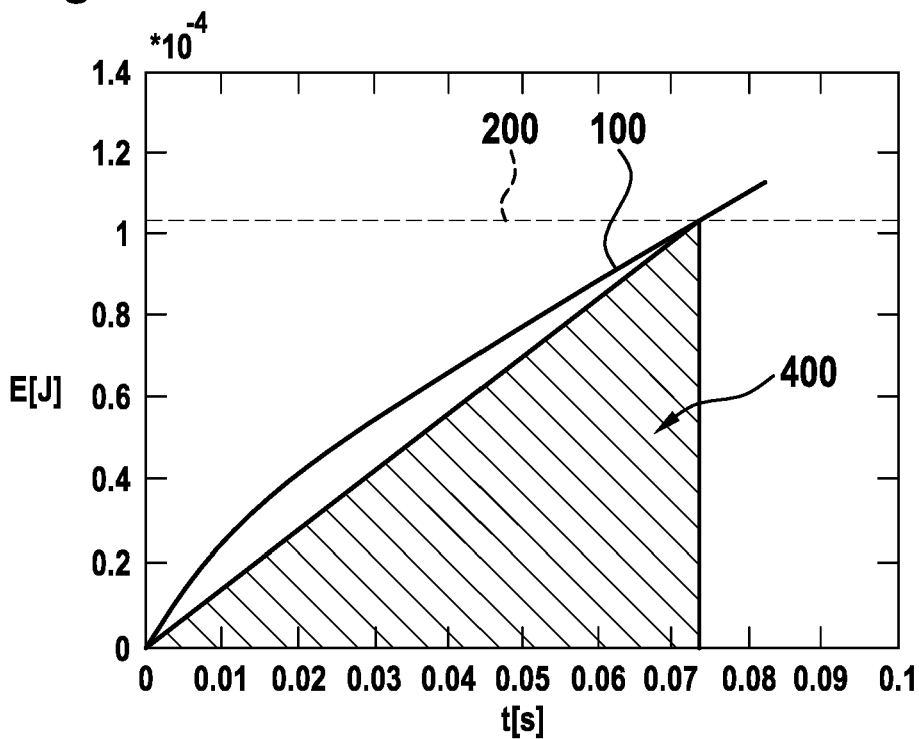
FIG. 6 shows a fourth schematic view of the derivation of the energy criterion.

FIG. 6 schematically shows the emitted pulse groups 400 in this regard until energy limit 200 of the pulse pattern is reached.

The above-described simplifications thus make it possible to emit pulse groups at a certain interval, while an energy limit per pulse pattern is monitored at the same time. The parameters of this simplification thus read as follows:

maximum permissible individual pulse energy
minimum permissible temporal individual pulse distance
maximum permissible number of individual pulses within a pulse group
minimum permissible interval between two pulse groups
maximum permissible energy limit per frame (maximum permissible pulse number per frame)

From a predefined pulse length and pulse power, the pulse energy of a planned laser pulse as well as of an emitted laser pulse may be derived. From this, the maximum permissible energy limit per pulse pattern may be calculated as described above. The minimum permissible individual pulse distance may be obtained from the time, when laser system 1 is a scanning system, during which the system emits pulses in an eye diameter without interruption. In this way, a maximum energy may be calculated which may be emitted during this time, from which the number of the laser pulses, and from which, in turn, the minimum permissible individual pulse distance, result. The number of the laser pulses, at the same time, corresponds to the maximum permissible number of individual pulses within a pulse group.

The minimum permissible interval between two pulse groups is calculated from the intersecting point of energy limit 100 with the maximum energy limit 200 per pulse pattern. All laser pulses which would raise the energy above energy limit 200 are already prevented by this mechanism. For this reason, a monitoring is ensured up until the point in time at which energy limit 200 is reached. The minimum permissible interval between two pulse groups may be ascertained from the point in time at which energy limit 200 is reached, the maximum permissible energy limit, and the pulse group parameters.

A safety distance may particularly advantageously be added to all used parameters. As a result, the limits of known eye safety standards are not immediately reached in the event of an error. A buffer therefore exists, which increases the eye safety of laser system 1.

With the aid of pseudo code, an example algorithm is represented hereafter to implement the example method according to the present invention on control unit 3:

```
// number of laser pulses in a pulse group
Initialize Macropixelarray groupPulseCounter = [0];
    // pause between two pulse groups
Initialize Macropixelarray groupPauseTimer = [0];
    // number of laser pulses per pulse pattern
Initialize Macropixelarray framePulseCounter = [0];
While Forever
{
```

-continued

```
If pulsePlanned == true
{
    // individual pulse criterion
pulsePermitted = checkPulseEnergy(pulse);
    // pause criterion between two individual pulses
pulsePermitted = pulsePermitted & checkPulsePause(previousPulse,
pulse);
    // discretization with the aid of pixels
Array pos = calculateAffectedMacropixels(pulse);
    // maximum number of pulses per pulse pattern or pulse
group
If framePulseCounter(pos)<FrameLimit and
groupPulseCounter(pos)<GroupLimit
{
pulsePermitted = pulsePermitted;
framePulseCounter(pos) = framePulseCounter(pos) + 1;
groupPulseCounter(pos) = groupPulseCounter(pos) + 1;
    // distance between two pulse groups
If groupPulseCounter(pos) == GroupLimit
{
groupPauseTimer(pos) = groupPauseTimer(pos) + GroupPause;
}
} else {
pulsePermitted = false;
}
}
For each pixel in groupPauseTimer( )
{
If groupPauseTimer(pixel) > 0
{
groupPauseTimer(pixel) = groupPauseTimer(pixel)–1;
} else {
groupPulsCounter(pixel) = 0;
}
}
If newFrame = true
{
framePulseCounter (all) = 0;
}
}
```

What is claimed is:

1. A method for emitting laser light in the form of laser pulses, the method comprising the following steps:
planning a laser pulse based on pulse parameters;
checking whether laser pulses which were emitted by a light detection and ranging (LIDAR) sensor within a predefined preceding time interval, together with the planned pulse, meet a predefined energy criterion;
emitting the planned laser pulse using the LIDAR sensor if the energy criterion is met, and not emitting the planned laser pulse or reducing a power of the laser pulse if the energy criterion is not met; and
at least one of the following (I)-(II):
(I) (i) determining, based on a present state of the LIDAR sensor, a maximum number of the laser pulses that are within a single set of the laser pulses that are able to strike an eye, at least a remaining number of the laser pulses within the single set being incapable of striking the eye, and (ii) based on the determination of the maximum number, determining a maximum permitted energy for the single set as at least a part of the energy criterion; and
(II) determining a maximum number of laser pulses that can be consecutively emitted while the LIDAR sensor operates at a defined angular range while maintaining a predefined minimum distance between each pair of temporally adjacent ones of the laser pulses, wherein:
(a) the energy criterion is based on the determined maximum number; and/or
(b) the determined maximum number forms a pulse group, and the method further comprises (i) determining a minimum time delay between consecutive outputs of instances of the pulse group, and (ii) controlling output of the LIDAR sensor based on the determined minimum time delay.

2. The method as recited in claim 1, wherein the energy criterion represents a maximum energy of the laser light which does not result in permanent damage to a human eye.

3. The method as recited in claim 1, wherein all of the laser pulses are discrete laser pulses having a predefined minimum distance.

4. The method as recited in claim 1, wherein the energy criterion includes (i) a maximum value of a permitted pulse duration and/or pulse energy of the planned laser pulse, and/or (ii) a minimum value of a distance between two laser pulses.

5. The method as recited in claim 1, wherein a predefined pulse pattern is emitted in a recurring manner.

6. The method as recited in claim 5, wherein the energy criterion includes a maximum value of an emission energy of the entire predefined pulse pattern.

7. The method as recited in claim 1, wherein the laser light is emitted in a scanning manner at a changing solid angle, the solid angle being discretized in a grid made up of discrete pixels, a light output of each laser pulse striking the pixel being integrated for each pixel, and it being checked that each pixel meets the energy criterion.

8. The method as recited in claim 7, wherein a time period is determined during which the laser light passes over a predefined eye opening area, a pulse group of multiple laser pulses being emittable during the time period, and the energy criterion having a maximum value for the laser pulses of the pulse group and/or for a distance between two pulse groups.

9. The method as recited in claim 1, wherein the pulse parameters include a pulse point in time and/or a pulse energy and/or a pulse length and/or a pulse power and/or a pulse exit angle.

10. A non-transitory machine-readable memory medium on which is stored a computer program including program code for emitting laser light in the form of laser pulses, the computer program, when executed by a computing device, causing the computing device to perform a method, the method comprising:
planning a laser pulse based on pulse parameters;
checking whether laser pulses which were emitted by a light detection and ranging (LIDAR) sensor within a predefined preceding time interval, together with the planned pulse, meet a predefined energy criterion;
emitting the planned laser pulse using the LIDAR sensor if the energy criterion is met, and not emitting the planned laser pulse or reducing a power of the laser pulse if the energy criterion is not met; and
at least one of the following (I)-(II):
(i) determining, based on a present state of the LIDAR sensor, a maximum number of the laser pulses that are within a single set of the laser pulses that are able to strike an eye, at least a remaining number of the laser pulses within the single set being incapable of striking the eye, and (ii) based on the determination of the maximum number, determining a maximum permitted energy for the single set as at least a part of the energy criterion; and
(II) determining a maximum number of laser pulses that can be consecutively emitted while the LIDAR sensor operates at a defined angular range while maintaining a predefined minimum distance between each pair of temporally adjacent ones of the laser pulses, wherein:
(a) the energy criterion is based on the determined maximum number; and/or
(b) the determined maximum number forms a pulse group, and the method further comprises (i) determining a minimum time delay between consecutive outputs of instances of the pulse group, and (ii) controlling output of the LIDAR sensor based on the determined minimum time delay.

11. A laser system for emitting laser light, comprising:
a light detection and ranging (LIDAR) sensor, wherein the LIDAR sensor is configured to emit laser pulses based on pulse parameters; and
a controller, wherein the controller is configured to:
plan a laser pulse based on pulse parameters;
check whether laser pulses which were emitted by the LIDAR sensor within a predefined preceding time interval, together with the planned pulse, meet a predefined energy criterion;
emit the planned laser pulse using the LIDAR sensor if the energy criterion is met, and not emit the planned laser pulse or reduce a power of the laser pulse if the energy criterion is not met; and
perform least one of the following (I)-(II):
(I) (i) determining, based on a present state of the LIDAR sensor, a maximum number of the laser pulses that are within a single set of the laser pulses that are able to strike an eye, at least a remaining number of the laser pulses within the single set being incapable of striking the eye, and (ii) based on the determination of the maximum number, determining a maximum permitted energy for the single set as at least a part of the energy criterion; and
(II) determining a maximum number of laser pulses that can be consecutively emitted while the LIDAR sensor operates at a defined angular range while maintaining a predefined minimum distance between each pair of temporally adjacent ones of the laser pulses, wherein:
(a) the energy criterion is based on the determined maximum number; and/or (b) the determined maximum number forms a pulse group, and the controller is further configured to (i) determine a minimum time delay between consecutive outputs of instances of the pulse group, and (ii) control output of the LIDAR sensor based on the determined minimum time delay.

12. The method as recited in claim 1, further comprising:
identifying a repeating pattern of emission of the laser pulses which were emitted, the pattern including a plurality of the laser pulses, wherein the checking includes, based on the identified pattern, determining a representation of an amount of energy produced by a single instance of the pattern, which is produced by a combination of energy output by all of the plurality of the laser pulses within the pattern.

13. The method as recited in claim 1, wherein the emitting is performed so that only discrete laser pulses are emitted without any continuous laser wave and without any modulated laser beams.

14. The method as recited in claim 1, further comprising:
the determining, based on the present state of the LIDAR sensor, of the maximum number of the laser pulses that are within the single set of the laser pulses that are able to strike the eye, the at least the remaining number of the laser pulses within the single set being incapable of striking the eye; and based on the determination of the maximum number, the determining of the maximum permitted energy for the single set as the at least the part of the energy criterion.

15. The method as recited in claim 1, comprising:
the determining of the maximum number of laser pulses that can be consecutively emitted while the LIDAR sensor operates at the defined angular range while maintaining the predefined minimum distance between the each pair of temporally adjacent ones of the laser pulses, wherein the energy criterion is based on the determined maximum number.

16. The method as recited in claim 1, further comprising:
the determining of the maximum number of laser pulses that can be consecutively emitted while the LIDAR sensor operates at the defined angular range while maintaining the predefined minimum distance between the each pair of temporally adjacent ones of the laser pulses, wherein the determined maximum number forms the pulse group;
the determining of the minimum time delay between the consecutive outputs of instances of the pulse group; and
the controlling of the output of the LIDAR sensor based on the determined minimum time delay.

17. The non-transitory machine-readable memory medium as recited in claim 10, wherein the method comprises:
the determining, based on the present state of the LIDAR sensor, of the maximum number of the laser pulses that are within the single set of the laser pulses that are able to strike the eye, the at least the remaining number of the laser pulses within the single set being incapable of striking the eye; and
based on the determination of the maximum number, the determining of the maximum permitted energy for the single set as the at least the part of the energy criterion.

18. The non-transitory machine-readable memory medium as recited in claim 10, wherein the method comprises the determining of the maximum number of laser pulses that can be consecutively emitted while the LIDAR sensor operates at the defined angular range while maintaining the predefined minimum distance between the each pair of temporally adjacent ones of the laser pulses, wherein:
the energy criterion is based on the determined maximum number; and/or
the determined maximum number forms the pulse group, and the method further comprises the determining of the minimum time delay between the consecutive outputs of instances of the pulse group, and the controlling of the output of the LIDAR sensor based on the determined minimum time delay.

19. The laser system as recited in claim 11, wherein the controller is configured to perform:
the determination, based on the present state of the LIDAR sensor, of the maximum number of the laser pulses that are within the single set of the laser pulses that are able to strike the eye, the at least the remaining number of the laser pulses within the single set being incapable of striking the eye; and
based on the determination of the maximum number, the determination of the maximum permitted energy for the single set as the at least the part of the energy criterion.

20. The laser system as recited in claim 11, wherein the controller is configured to perform the determination of the maximum number of laser pulses that can be consecutively emitted while the LIDAR sensor operates at the defined angular range while maintaining the predefined minimum distance between the each pair of temporally adjacent ones of the laser pulses, wherein:
- the energy criterion is based on the determined maximum number; and/or
- the determined maximum number forms the pulse group, and the controller is further configured to determine the minimum time delay between the consecutive outputs of instances of the pulse group, and control the output of the LIDAR sensor based on the determined minimum time delay.

* * * * *